United States Patent [19]

Adler et al.

[11] 4,106,327

[45] Aug. 15, 1978

[54] ANISOTROPIC DETERMINATION AND CORRECTION FOR ULTRASONIC FLAW DETECTION BY SPECTRAL ANALYSIS

[75] Inventors: Laszlo Adler, Knoxville; K. Von Cook, Clinton; William A. Simpson, Jr.; D. Kent Lewis, both of Knoxville, all of Tenn.

[73] Assignee: The United States of America as represented by the United States Department of Energy, Washington, D.C.

[21] Appl. No.: 853,947

[22] Filed: Nov. 22, 1977

[51] Int. Cl.² ............................................. G01N 29/00
[52] U.S. Cl. .................................. 73/1 DV; 73/597; 73/602; 73/618
[58] Field of Search ............. 73/1 DV, 597, 598, 602, 73/606, 618

[56] References Cited

U.S. PATENT DOCUMENTS

| 3,756,071 | 9/1973 | Dory | 73/602 |
| 3,776,026 | 12/1973 | Adler et al. | 73/602 |
| 3,812,709 | 5/1974 | Benson et al. | 73/597 |

*Primary Examiner*—James J. Gill
*Attorney, Agent, or Firm*—Dean E. Carlson; Stephen D. Hamel; Louis M. Deckelmann

[57] ABSTRACT

The anisotropic nature of a material is determined by measuring the velocity of an ultrasonic longitudinal wave and a pair of perpendicular ultrasonic shear waves through a sample of the material each at a plurality of different angles in three planes orthogonal to each other. The determined anisotropic nature is used as a correction factor in a spectral analyzing system of flaw determination.

10 Claims, 12 Drawing Figures

• • • EXPERIMENTAL
─── CALCULATED

LONGITUDINAL

SHEAR POLARIZED IN THE 1-2 PLANE

SHEAR POLARIZED IN THE 3 AXIS

•••EXPERIMENTAL
———CALCULATED

LONGITUDINAL

SHEAR POLARIZED IN THE 1-3 PLANE

SHEAR POLARIZED IN THE 2 AXIS

• • • EXPERIMENTAL
—— CALCULATED

LONGITUDINAL

SHEAR POLARIZED IN THE 2-3 PLANE

SHEAR POLARIZED IN THE 1 AXIS

ANISOTROPIC DETERMINATION AND CORRECTION FOR ULTRASONIC FLAW DETECTION BY SPECTRAL ANALYSIS

BACKGROUND OF THE INVENTION

The invention was made in the course of, or under, a contract with the U.S. Energy Research and Development Administration.

The present invention relates to an improvement over the U.S. Pat. No. 3,662,589, issued May 16, 1972, and No. 3,776,026, issued Dec. 4, 1973 to Laszlo Adler, et al, both entitled "Ultrasonic Flaw Determination by Spectral Analysis", and both having a common assignee with the present application.

The above patents relate to a nondestructive method for determining the size and orientation of a randomly oriented flaw within a material sample comprising the steps of generating an ultrasonic pulse having a wide frequency spectrum by a transducer, receiving with the same transducer (or another transducer) ultrasonic signals reflected from any flaw in said sample in close proximity to said transducer, analyzing the frequency spectrum of the reflected signals to determine a first average frequency interval between points of maxima in the reflected spectrum, recording said first average frequency interval, displacing the transducer a first selected angle in a first plane from its first position with respect to the sample and then repeating the above steps to determine a second average frequency interval between points of maxima in the second reflected spectrum, recording said second average frequency interval, displacing the transducer a second selected angle in a second plane and from said first position with respect to said sample and then repeating the above steps to determine a third average frequency interval between points of maxima in the third reflected spectrum, recording said third average frequency interval, and finally utilizing the recorded average frequency intervals obtained for all positions of said transducer for determining the size and orientation of the flaw in said sample.

The above patented method, however, has been found to give erroneous results when inspecting welds, particularly in thick sections of stainless steel and like materials useful for nuclear reactor systems. Frequently, the size and location, as obtained by the above method, are found to be substantially in error when compared to destructive analysis. Thus, the ultrasonic inspection with the above prior art appeared to be non-applicable to the inspection of thick welds in pipe, plate, and other configurations.

In the prior research, materials under study were isotropic or were assumed to be so. Under such conditions, ultrasound velocities are substantially uniform in any direction of propagation. In recent work, however, it has been found that weld metal is anisotropic, i.e., nonisotropic, and thus there is a slowing down of the ultrasound in certain directions of propagation through a sample of such material. This is deemed to create the erroneous results obtained heretofore.

Thus, there exists a need for determining the true and/or actual velocity of sound propagation through any given nonisotropic sample material at the angle of transducer orientation, and applying such a velocity correction to the above method to thus provide a more accurate determination of the flaw size and its location.

The present invention was conceived to meet this need in a manner to be described hereinbelow.

SUMMARY OF THE INVENTION

It is the object of the present invention to provide a means and/or a method for determining the actual velocity of sound propagation through any given nonisotropic sample material at the angle of transducer orientation such that a more accurate determination of the flaw size and its location can be made.

The above object has been accomplished in the present invention by providing a means and/or method for accurately determining various ultrasound velocities through a sample as a function of respective orientations such that a desired or selected one of such velocities can then be utilized for correctly determining the size of any flaw and the orientation of such a flaw in a sample material in a manner to be described hereinbelow.

DESCRIPTION OF THE PREFERRED EMBODIMENT

In the U.S. Pat. Nos. 3,662,589 and 3,776,026, referred to above, the principal equation used in the spectral analysis for flaws is:

$$\Delta f = \frac{v}{[2(\sin^2 \theta_2 + \cos^2 \theta_2 \sin^2 \theta_1)^{\frac{1}{2}}]d}, \text{ where}$$

$d$ = diameter of reflector (flaw)
$v$ = velocity of sound in the material,
$\Delta f$ = average frequency interval between points of maxima in reflected spectrum, and
$\theta_1, \theta_2$ = angles at which $\Delta f$ is obtained.

Since it has been determined that the ultrasound velocities through anisotropic material, such as weld metal, are not uniform in all directions of propagation, as discussed hereinabove, and since such a variation of ultrasound velocity as a function of polar orientation will have a significant effect upon the determination of flaw size and orientation when ultrasonic spectral analysis is used for detecting the flaw, a means and method for accurately determining the ultrasound velocity (the value v in the above equation) in such an anisotropic material as a function or orientation will now be discussed.

Figure 1:
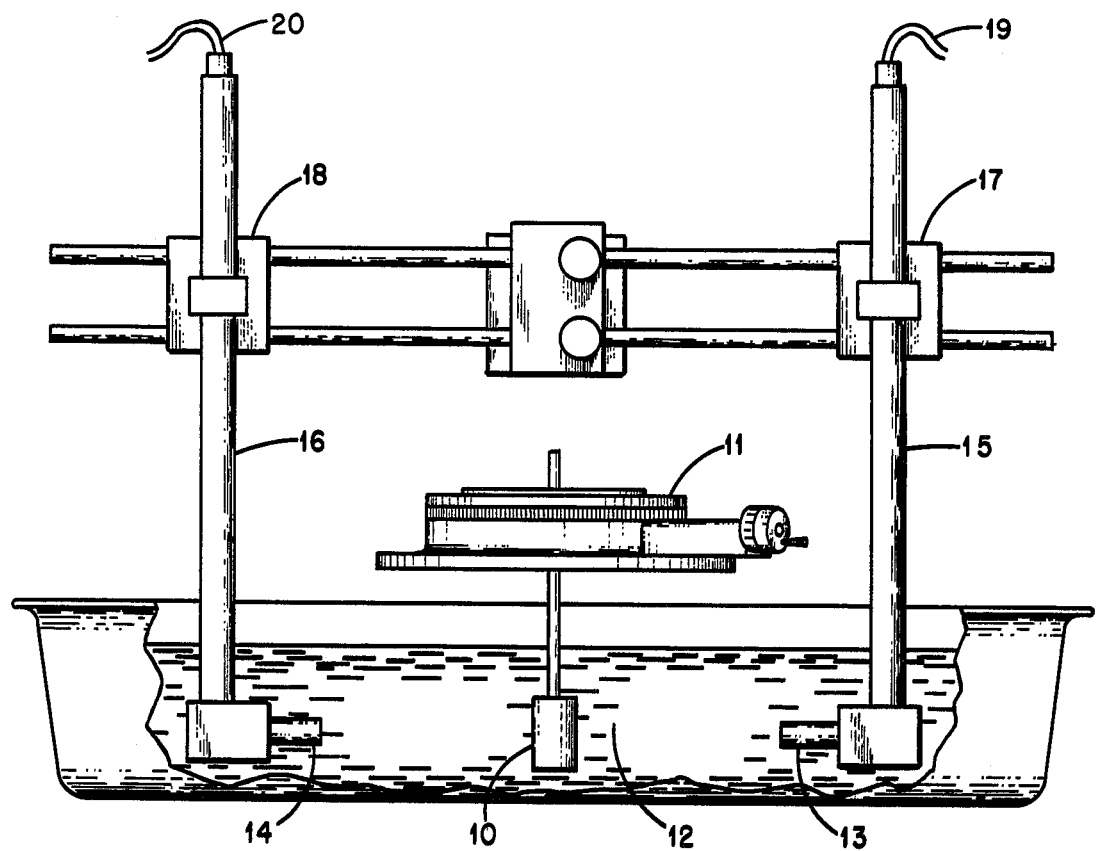
FIG. 1 is a drawing illustrating apparatus for measuring ultrasound velocity propagation in samples.

Referring now to FIG. 1, a system is illustrated for the determination of ultrasound velocities through a sample as a function of orientation. A sample 10, in this instance a cylinder, is mounted from a goniometer 11, whereby the sample 10 is adapted to be slowly rotated about its axis while maintained within a sound-coupling liquid 12, such as water. Also disposed in the liquid 12 is an ultrasound transmitter 13 and a receiver 14. The transmitter 13 and receiver 14 are adjustable by means of tubes 15, 16, respectively, and by manipulators 17, 18, respectively, so as to be aligned with the sample 10 for through transmission measurements. The receiver 14 or the transmitter 13 is adapted to be moved to other locations to obtain ultrasonic velocities. Electrical lead 19 supplies the transmitter 13 while lead 20 carries signals from the receiver 14 to monitoring and recording equipment, not shown.

Figure 2:
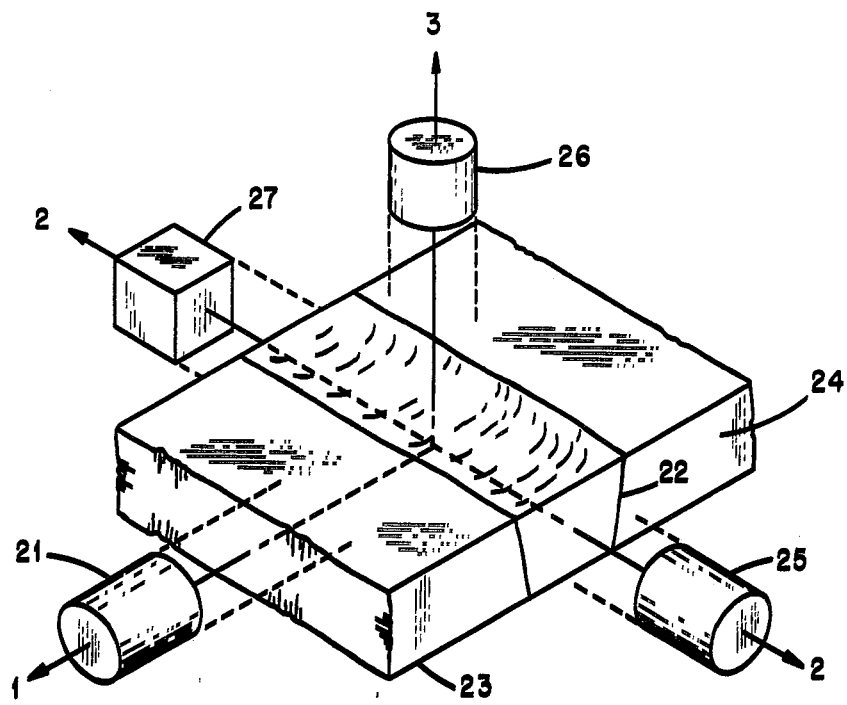
FIG. 2 is an isometric drawing showing sample orientations in weldment.

The manner of obtaining samples of a weldment for use in equipment such as shown in FIG. 1, is illustrated in FIG. 2 of the drawings. One cylindrical sample 21 is obtained having its axis along the No. 1 axis, i.e., across the width of the weld 22 from the base material 23 to the base material 24. Another cylindrical sample 25 is prepared having its axis along the weld 22 on the No. 2 axis. A third cylindrical sample 26 is obtained having its axis through the weld 22 on the No. 3 axis. A cubical (or rectangular) sample 27 may be prepared having faces perpendicular to the above-mentioned, mutually-perpendicular axes and is useful for calibration purposes.

Figure 3A:
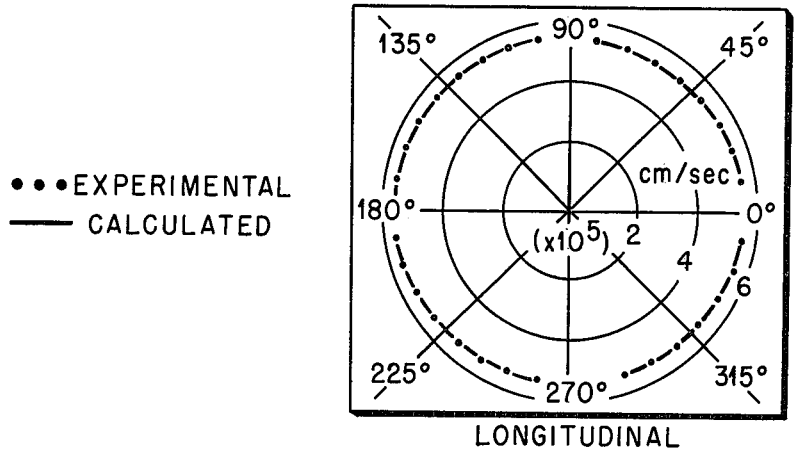
FIGS. 3a, 3b, and 3c are an assembly of polar plots showing the variation of ultrasonic velocity as a function of orientation in one of the major planes illustrated in FIG. 2 for an Inconel 82 weldment.
Figure 3B:
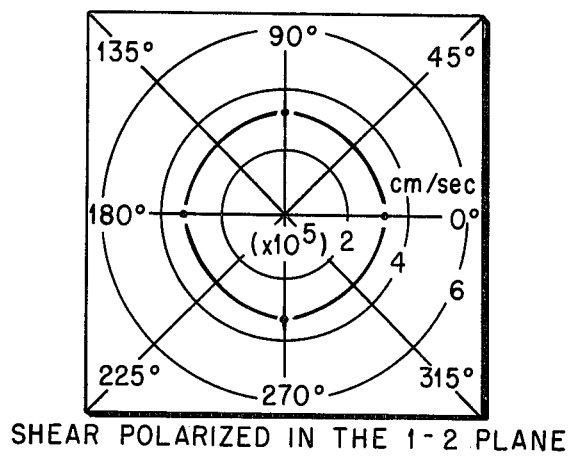
Figure 3C:
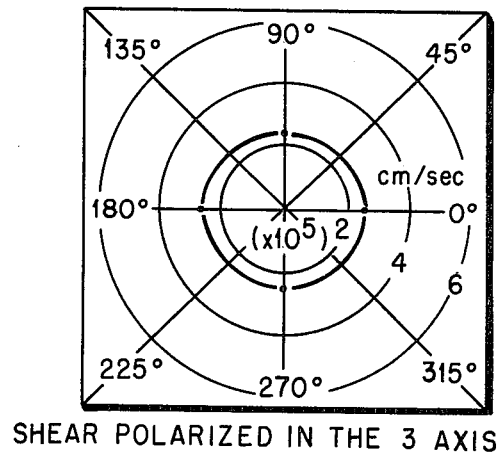
Figure 4A:
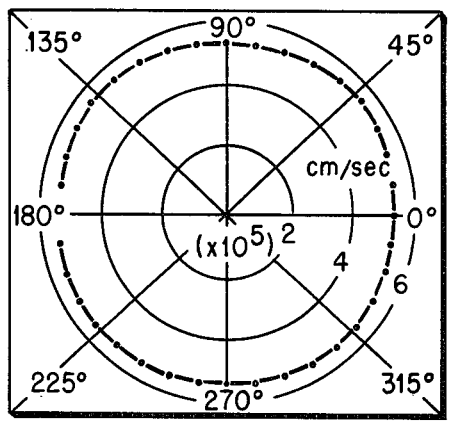
FIGS. 4a, 4b, and 4c are an assembly of polar plots showing the variations of ultrasonic velocity as a function of orientation in another of the major planes illustrated in FIG. 2 for an Inconel 82 weldment.
Figure 4B:
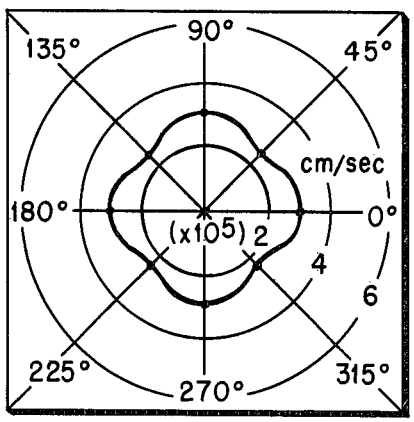
Figure 4C:
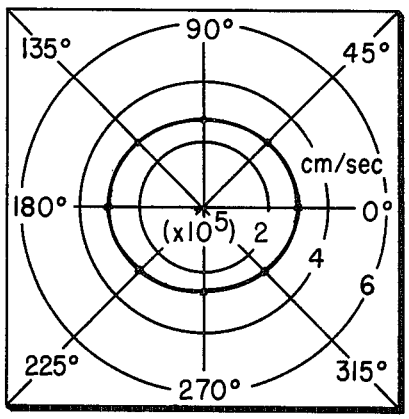
Figure 5A:
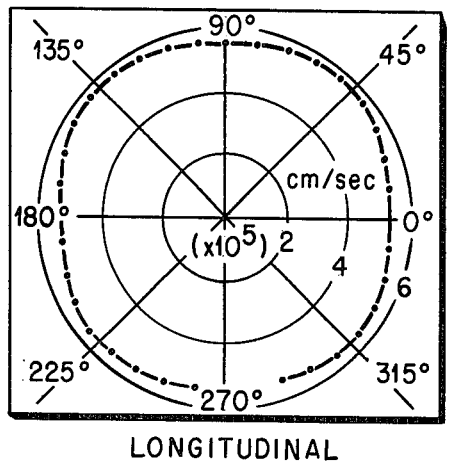
FIGS. 5a, 5b, and 5c are an assembly of polar plots showing the variation of ultrasonic velocity as a function of orientation in still another of the major planes illustrated in FIG. 2 for an Inconel 82 weldment.
Figure 5B:
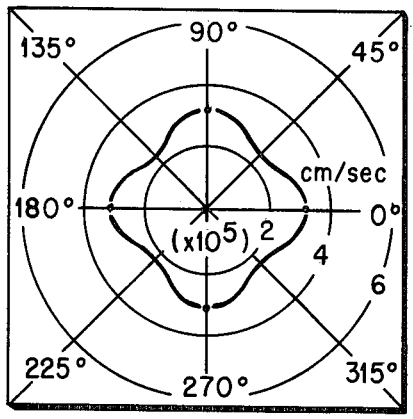
Figure 5C:
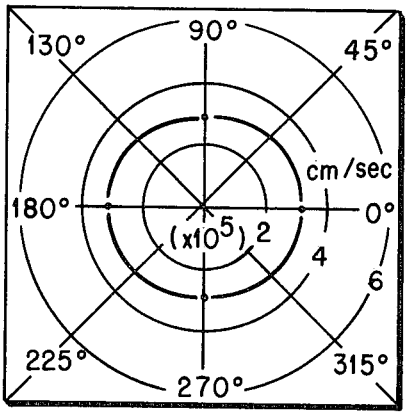

Typical data for the samples in FIG. 2, when examined with the apparatus of FIG. 1, are depicted in the polar plots of FIGS. 3a–3c, 4a–4c, and 5a–5c. These are from an Inconel 82 weldment. The plots of FIGS. 3a–3c represent data that would be generated using a cylindrical sample such as sample 26 of FIG. 2. The longitudinal data of FIG. 3a is obtained by through-transmission directly across a diameter of the sample; the polar plot of FIG. 3b is the signal derived by the shear wave polarized in the 1-2 plane of FIG. 2; and the third polar plot of FIG. 3c is the shear wave polarized along the No. 3 axis. Similarly, the plots of FIGS. 4a–4c are representative of a cylinder such as sample 25 of FIG. 2, and the plots of FIGS. 5a–5c are representative of a cylinder like sample 21. The points on the plots are actual data (in the shear plots, the data actually came from a cube such as sample 27), while the solid lines are derived from calculations. A sample taken through the thickness of the weld (like sample 26) exhibited little variation of ultrasound velocity as a function of polar angle. However, the other samples exhibited changes in velocity of up to 30%. This clearly demonstrates that the weld material is anisotropic even though the base material itself is essentially isotropic. It should be noted that variations up to 40% have been measured in other anisotropic materials.

The most common analysis of welds uses a 45° polarized shear wave. As may be seen in FIG. 4b and 5b, this angle correlates with the maximum variation in the propagation velocity and thus the greatest error caused by anisotropy.

Figure 6:
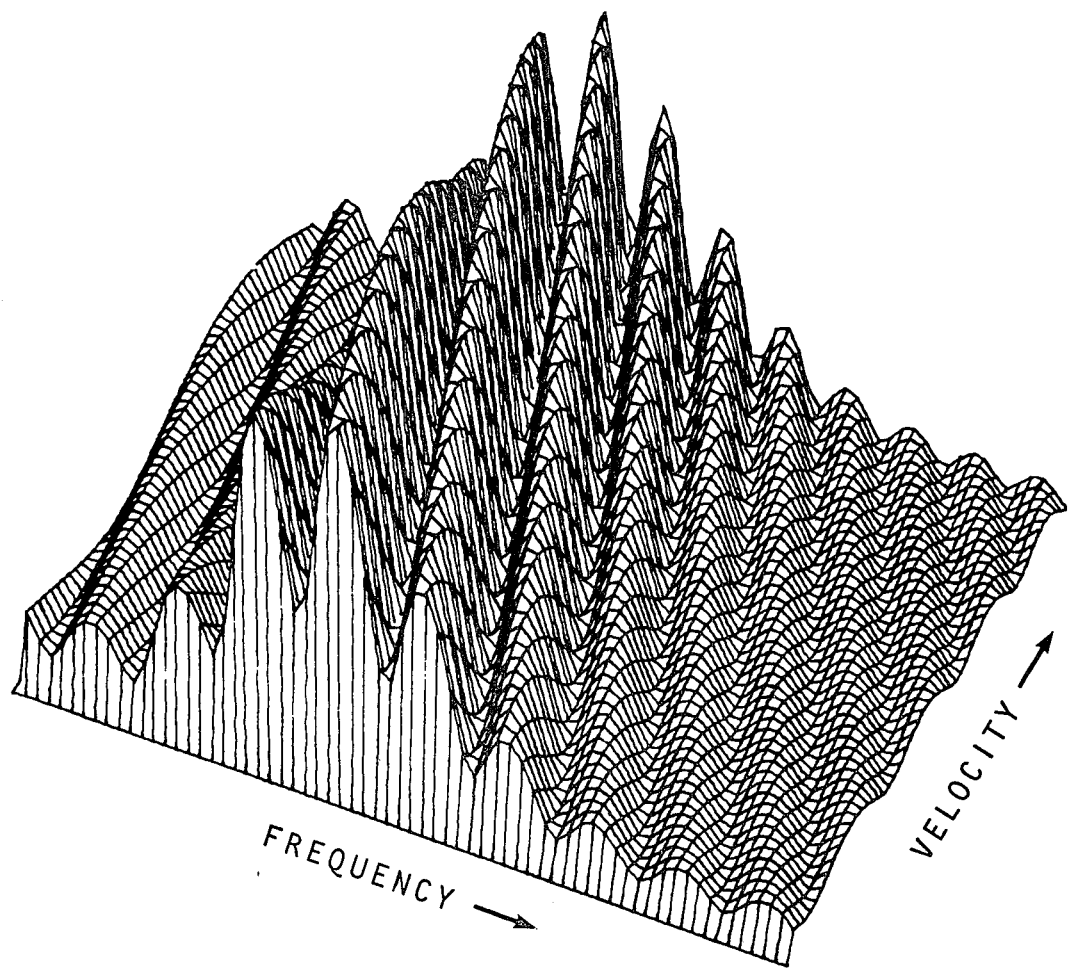
FIG. 6 is a reconstructed three dimensional plot of the interference reflected spectrum of a weld containing a flaw showing the effect of angle of orientation.

The effect of a varying velocity of sound is illustrated in FIG. 6 of the drawings. In this pseudo-3D computer generated plot, the spectrum in the foreground is that which would be obtained by spectral analysis from a 0.25 inch diameter circular flaw in type 308 stainless steel if the velocity was that of the base metal. The spectrum in the background is the true distribution when account is taken of the anisotropy; i.e., the distribution that would be measured. This demonstrates the necessity of correcting for velocity variations in the welds.

Accordingly, before welds in a particular base material are to be analyzed for flaws by the spectral analysis method, the values of propagation velocity must be obtained. This is accomplished through the use of representative samples as described above. The velocity plots from the samples are then used to determine the proper value of velocity to be used in the calculation of flaw size and its orientation using the methods described in the above-mentioned prior art patents. The data from a set of samples for a specific material may then be used for subsequent welds of that material.

In addition to welds, other materials have been found to be anisotropic. For example, cast metals generally exhibit anisotropy. Also, some graphite structures are known to be anisotropic. Accordingly, a proper set of velocity propagation plots would be required in order to utilize ultrasonic spectral analysis for flaws in such structured materials.

Initial testing of the improved spectral analysis method utilizing the proper velocity in the calculations for flaw identification yielded data in good agreement with findings by destructive analysis. However, without the application of a proper value of velocity, flaws in thick objects are often indicated which are not found when physical inspections are made.

This invention has been described by way of illustration rather than by limitation and it should be apparent that it is equally applicable in fields other than those described.

What is claimed is:

1. A method for determining the true velocity of sound in an anisotropic material as a function of orientation comprising the steps of obtaining a plurality of respective samples of said material along at least three mutually perpendicular axes therethrough, sequentially positioning each of said respective samples between an ultrasonic transmitter and an ultrasonic receiver in a sound coupling liquid, slowly rotating each of said samples during the time each sample is positioned between said transmitter and receiver, sequentially deriving a series of polar plots as a function of orientation from the output of said ultrasonic receiver for each of said samples during the time each of said rotating samples is in position between said transmitter and receiver, and determining said true velocity of sound in said anisotropic material for a desired orientation from said polar plots, whereby said true velocity can subsequentially be utilized in a spectral analysis method for quantitatively determining the size and location of flaws within another sample of said material.

2. The method set forth in claim 1, wherein said desired orientation is a 45° polarized shear wave obtained from one series of said plots.

3. The method set forth in claim 2, wherein said sound coupling liquid is water.

4. The method set forth in claim 1, wherein said obtained samples are cylindrical.

5. The method set forth in claim 1, and further including the further steps of obtaining a cubical sample of said anisotropic material having faces perpendicular to said mutually perpendicular axes, positioning said cubical sample between said transmitter and receiver, and deriving a series of further polar plots as a function of orientation from the output of said receiver during the time said cubical sample is between said transmitter and receiver, said polar plots derived from said cubical sample adapted to be utilized for calibration purposes.

6. In a first nondestructive method for determining the size and orientation of a randomly oriented flaw within a materials sample comprising the steps of generating an ultrasonic pulse having a wide frequency spectrum by a transducer, receiving with a transducer ultrasonic signals reflected from any flaw in said sample in close proximity to said receiving transducer, analyzing the frequency spectrum of the reflected signals to determine a first average frequency interval between points of maxima in the reflected spectrum, recording said first average frequency interval, displacing the transducer a first selected angle in a first plane from its first position with respect to the sample and then repeating the above steps to determine a second average frequency interval between points of maxima in the second reflected spectrum, recording said second average frequency interval, displacing the transducer a second selected angle in a second plane and from said first position with respect to said sample, and then again repeating the above steps to determine a third average frequency interval between points of maxima in the third reflected spectrum, recording said third average frequency interval, and finally utilizing the recorded average frequency intervals obtained for all positions of said transducer for determining the size and orientation of the flaw in said sample, said recorded average frequency intervals being a function of the velocity of sound in said sample material, the improvement comprising the further method for determining the true velocity of sound in said material as a function of orientation when said material is anisotropic, comprising the steps of obtaining a plurality of respective samples of said anisotropic material along at least three mutually perpendicular axes therethrough, sequentially positioning each of said respective samples between an ultrasonic transmitter and an ultrasonic receiver in a sound coupling liquid, slowly rotating each of said samples during the time each sample is positioned between said transmitter and receiver, sequentially deriving a series of polar plots as a function of orientation from the output of said ultrasonic receiver for each of said samples during the time each of said rotating samples is in position between said transmitter and receiver, determining said true velocity of sound in said anisotropic material for a desired orientation from said polar plots, and utilizing the determined true velocity of sound in said antisotropic material for thus providing an accurate determining of the size and orientation of any flaw in the anistropic material in accordance with said first method.

7. The method set forth in claim 6, wherein said pulse generating transducer and said receiving transducer are the same transducer.

8. The method set forth in claim 6, wherein said receiving transducer and pulse generating transducer are separate transducers.

9. The method set forth in claim 6, wherein said desired orientation is a 45° polarized shear wave obtained from one series of said polar plots.

10. The method set forth in claim 6, wherein said sound coupling liquid is water, and said obtained samples are cylindrical.

* * * * *